United States Patent [19]

Benefiel et al.

[11] 3,967,949

[45] July 6, 1976

[54] FLUOROALKOXYPHENYL-SUBSTITUTED NITROGEN HETEROCYCLES AS PLANT STUNTING AGENTS

[75] Inventors: Robert Lee Benefiel, Manila; Eriks Viktors Krumkalns, Indianapolis, both of Ind.

[73] Assignee: Eli Lilly and Company, Indianapolis, Ind.

[22] Filed: June 18, 1973

[21] Appl. No.: 371,106

[52] U.S. Cl. .................................. 71/76; 71/88; 71/92; 71/94; 260/250 B; 260/251 R; 260/290 R; 260/294.8 R; 260/295 R; 260/297 R; 260/297; 260/340.5; 260/340.7; 260/591; 260/592
[51] Int. Cl.² .................................. A01N 5/00
[58] Field of Search .................... 71/92, 94, 76

[56] References Cited
UNITED STATES PATENTS 3,781,369   12/1973   Larsen et al. ........................ 71/124
3,818,009   6/1974    Taylor et al. ........................ 71/92

FOREIGN PATENTS OR APPLICATIONS 1,935,292   1/1971   Germany ............................ 71/92

OTHER PUBLICATIONS

Einert, "Reduction in Last Internode Elongation, etc.," (1971) CA 76 No. 31207w. (1972).

Leopold, "Antagonism of Some Gibberellin etc.," (1971) CA 76 No. 31187q. (1972).

Primary Examiner—Glennon H. Hollrah
Attorney, Agent, or Firm—Dwight E. Morrison; Everet F. Smith

[57] ABSTRACT

There is disclosed a class of fluoroalkoxyphenyl-substituted nitrogen-containing heterocycles which are useful as herbicides, plant fungicides, and plant growth regulators. Internodal elongation of plants is inhibited by treatment with compounds of this invention.

9 Claims, No Drawings

Plant stunting agents# FLUOROALKOXYPHENYL-SUBSTITUTED NITROGEN HETEROCYCLES AS PLANT STUNTING AGENTS

BACKGROUND OF THE INVENTION

Methods and substances useful for the control of the height of plants have been the subject of much research for many years. Such control is of great economic benefit in many instances.

In the prior art, Margot et al., U.S. Pat. No. 2,839,446 (June 17, 1958), teach novel pyrimidines which are said to possess fungicidal activity. The Margot et al. compounds are distinguished by having at least one trichloromethane sulphenylmercapto group preferably attached at the 2-position of the pyrimidine ring.

In addition, Ballard et al., U.S. Pat. No. 2,658,895 (Nov. 10, 1958), teach 2-alkylphenyl-3,4,5,6-tetrahydropyrimidines, which are alleged to have fungicidal and detergent properties, and also are alleged to have use as asphalt additives.

Schellenberger et al., Angew. Chem. 76 (5), 226–7 (1964), teach the use of 2-methyl-5-hydroxymethylpyrimidine as an intermediate in the synthesis of a cocarboxylase inhibitor. This pyrimidine compound has the $R^1$ and $R^2$ substituents equal to hydrogen in the generic formula shown below, and, in our tests, has been found to be inactive both as a plant fungicide and as a plant growth regulator.

Bredereck et al., Chem. Ber., 93, 230–35 (1960), teach the preparation of 5-isopropylpyrimidine and 5-isoheptylpyrimidine, respectively. No utility is disclosed therefor.

Lewin et al., Arch. Biochem. and Biophysics, 101, 197–203 (1963), teach the use of 5-hydroxymethylpyrimidine as a substrate in studying the in vivo inhibition of thiamine synthesis.

Belgian Patent No. 714,003 (Oct. 22, 1968), teaches a series of 5-pyrimidinemethanols as being useful as plant fungicides and growth regulators.

Also in the prior art, Behun et al., Jour. Org. Chem., 26, 3379 (1961), teach the synthesis of 2-diphenylmethylpyrazine; however, there is no teaching of utility for the compound.

Klein et al., Jour. Org. Chem., 29 2623 (1964), teach only the method of synthesis of 2-ethoxy-3-pyrazinemethanol. No utility is alleged for the compound.

Rutner et al., Jour. Org. Chem., 28, 1898 (1963), teach the preparation of pyrazylmethanol, but not utility is alleged therefor.

Akkerman et al., Netherlands No. 105,432 (July 15, 1963), teach the preparation of α,α-diphenyl-2-pyrazineacetonitrile and α,α-diphenyl-2-pyrazineacetamide, which compounds are alleged to possess sedative and anticonvulsant properties.

Taylor et al., U.S. Pat. No. 3,544,682 (Dec. 1, 1970) teach the use of substituted pyrazines to control plant pathogenic fungi.

Hirschberg et al., Jour. Heterocyclic Chem., 2, 209 (1965), teach the preparation of 2-(3,6-dimethylpyrazinyl)-phenylcarbinol and homologues. However, no utility for the compounds is taught.

Additionally in the prior art, Sperber et al., U.S. Pat. No. 2,727,895 (Dec. 20, 1955), teach that certain 4-substituted pyridines, and the piperidines produced therefrom by hydrogenation of the pyridine ring, are useful primarily as anticonvulsants, and secondarily, as antibacterials and amtifungals, when administered in a variety of the usual pharmaceutical forms, such as tablets, elixirs, solutions and capsules. Thus, the Sperber et al. compounds are directed toward use in animals or humans.

Another prior art reference is Hoffmann et al., U.S. Pat. No. 3,153,046 (Oct. 13, 1964), which teaches dialkylpiperidylmethanols as having fungicidal, and especially antibacterial, properties useful against Microsporum audouini, Trichophyton interdigitalis, and Staphylococcus aureus, and against tubercle bacilli. Hoffmann et al. teach that their compounds can be used as disinfectants, preservatives, or as medicaments for the treatment of bacterial infections, and thus the compounds are implicitly directed to use in humans or animals.

Duerr et al., U.S. Pat. No. 3,203,855 (Aug. 31, 1965), teach a method for combatting phytopathogenic organisms, i.e., fungi or bacteria, using the compound 2-(2,2,2-trichloro-1-hydroxyethylamino)pyridine, which compound differs significantly from those described in the instant application.

Also in the prior art is Van Heyningen, U.S. Pat. No. 3,396,224 (Aug. 6, 1968), which teaches that substituted 3-pyridylmethane derivatives are active against phytopathogenic fungi. The compounds disclosed by Van Heyningen have shown most activity against airborne fungi, little or no activity against soil-borne fungi, and minimal activity as plant growth regulators.

SUMMARY

The present invention relates to a class of novel fluoroalkoxyphenyl-substituted nitrogen-containing heterocycles. These novel compounds have been found effective as plant growth regulators. Internodal elongation of crop plants, ornamental plants, woody plants and turf is inhibited by treatment with these novel compounds at a rate of about 0.125 to about 5 lbs./A. Such treatment does not injure the plants.

DESCRIPTION OF THE PREFERRED EMBODIMENT

It is an object of this invention to provide novel fluoroalkoxyphenyl-substituted nitrogen-containing heterocyclic compounds, as well as methods for the use of and compositions containing such compounds, which methods and compositions are useful for regulating the growth of crop plants, ornamental plants, woody plants, and turf.

In fulfillment of this object, this invention provides novel compounds of the class represented by the formula

I wherein
R is 2-pyrazinyl, 3-pyridyl, or 5-pyrimidinyl;
$R^1$ is phenyl, pyridyl, $C_1$–$C_{12}$ alkyl, or $C_3$–$C_8$ cycloalkyl;
$R^2$ is trifluoromethoxyphenyl, tetrafluoroethoxyphenyl, pentafluoroethoxyphenyl, 3,4-(difluoromethylenedioxy)phenyl, or 2,2,4,4-tetrafluoro-1,3-benzodioxanyl;

X is hydrogen, hydroxy, lower alkoxy, lower alkylthio, or lower alkanoyloxy; and the nonphytotoxic acid addition salts thereof.

In the above formula I, $C_1$–$C_{12}$ alkyl can be any branched or straight chain saturated hydrocarbon radical, such as methyl, ethyl, n-propyl, isopropyl, n-butyl, isobutyl, sec.-butyl, tert.-butyl, n-amyl, isoamyl, sec.-amyl, tert.-amyl, n-hexyl, isohexyl, sec.-hexyl, n-heptyl, isoheptyl, sec.-heptyl, n-octyl, isooctyl, sec.-octyl, n-nonyl, isononyl, n-decyl, isodecyl, n-undecyl, isoundecyl, n-dodecyl, isododecyl, and the like.

Pyridyl for $R^1$ refers to 2-pyridyl, 3-pyridyl, and 4-pyridyl.

$C_3$–$C_8$ cycloalkyl refers to a monocyclic, saturated hydrocarbon radical, and includes cyclopropyl, cyclobutyl, cyclopentyl, cyclohexyl, cycloheptyl, and cyclooctyl.

Lower alkoxy refers to $C_1$–$C_4$ alkoxy and includes methoxy, ethoxy, n-propoxy, isopropoxy, n-butoxy, sec.-butoxy, isobutoxy, and t-butoxy.

Lower alkylthio refers to $C_1$–$C_4$ alkylthio and includes methylthio, ethylthio, n-propylthio, isopropylthio, n-butylthio, sec.-butylthio, t-butylthio and isobutylthio.

Lower alkanoyloxy refers to $C_2$–$C_5$ alkanoyloxy and includes acetyloxy, propionyloxy, butyryloxy, and valeryloxy.

While the novel compounds of the present invention have been defined in terms of a structural formula which depicts the structural features of the compounds used, and which indicates the presence therein of certain well-known organic radicals, including alkyl, cycloalkyl, pyridyl, pyrimidyl, pyrazinyl, and phenyl, it will be recognized by those skilled in the art that such radicals may bear one or more substituents without departing in any way from the spirit of the invention and without altering the properties of the compounds in such a way as would set them apart from the invention or take them outside its scope. Compounds having the structure depicted by the generic formula, supra, and bearing such substituents are accordingly considered as equivalents of the unsubstituted compounds. Among such substituent atoms and radicals are halo, hydroxy, nitro, lower alkyl, trifluoromethyl, methoxy, methylmercapto, cyano, hydroxymethyl, β-hydroxyethyl, acetyl, acetamido, and the like. It is to be fully understood that all compounds coming within the scope of the generic formula I, supra, contain a fluoroalkoxyphenyl moiety, represented by $R^2$, supra.

Suitable nonphytotoxic acid addition salts of those compounds coming within the scope of the generic formula, supra, and sufficiently basic to allow formation of such salts, can be prepared, employing, for example, the following acids: hydrochloric, hydrobromic, sulfuric, phosphoric, nitric, oxalic, p-toluenesulfonic, benzenesulfonic, methanesulfonic, maleic and the like. It will be understood by those skilled in the art that suitable salts include those which are not substantially more phytotoxic than the free bases from which they are derived.

Compounds coming within the scope of the generic formula, supra, include, but are not limited to the following:

α-Methyl-α-[p-(trifluoromethoxy)phenyl]-5-pyrimidinemethanol

α-Ethyl-α-[p-(pentafluoroethoxy)phenyl]-5-pyrimidinemethanol

α-Methyl-α-[p-(trifluoromethoxy)phenyl]-2-pyrazinemethanol

α-Ethyl-α-[p-(pentafluoroethoxy)phenyl]-2-pyrazinemethanol

α-[p-(Pentafluoroethoxy)phenyl]-α-(n-propyl)-3-pyridinemethanol hydrochloride

α-[3,4-(Difluoromethylenedioxy)phenyl]-α-(n-heptyl)-5-pyrimidinemethanol

α-(n-Octyl)-α-[p-(1,1,2,2-tetrafluoroethoxy)-phenyl]-3-pyridinemethanol hydrobromide α-Isobutyl-α-[p-(1,1,2,2-tetrafluoroethoxy)phenyl]-2-pyrazinemethanol sulfate α-Isopropyl-α-(2,2,4,4-tetrafluoro-1,3-benzodioxan-6-yl)-5-pyrimidinemethanol α-(n-Pentyl)-α-[p-(trifluoromethoxy)phenyl]-2-pyrazinemethanol α-(n-Nonyl)-α-[p-(trifluoromethoxy)phenyl]-5-pyrimidinemethanol methanesulfonate α-(n-Dodecyl)-α-[p-(1,1,2,2-tetrafluoroethoxy)-phenyl]-3-pyridinemethanol oxalate α-(n-Decyl)-α-[p-(trifluoromethoxy)phenyl]-5-pyrimidinemethanol α-Cyclopropyl-α-[p-(1,1,2,2-tetrafluoroethoxy)-phenyl]-3-pyridinemethanol α-Cyclobutyl-α-[p-(trifluoromethoxy)phenyl]-2-pyrazinemethanol α-Cyclopentyl-α-[p-(pentafluoroethoxy)phenyl]-5-pyrimidinemethanol α-(p-Tolyl)-α-[p-(trifluoromethoxy)phenyl]-3-pyridinemethanol α-(Valeryloxy)-α-(sec.-butyl)-α-[p-(1,1,2,2-tetrafluoroethoxy)phenyl]-5-methylpyrimidine α-(α,α,α,-Trifluoro-m-tolyl)-α-[p-(trifluoromethoxy)-phenyl]-2-pyrazinemethanol α-Cyclooctyl-α-[p-(pentafluoroethoxy)phenyl]-2-pyrazinemethanol α-(p-Tolyl)-α-[p-(trifluoromethoxy)phenyl]-3-pyridylmethane α-(α,α,α-Trifluoro-m-tolyl)-α-[p-(trifluoromethoxy)-phenyl]-2-pyrazinylmethane α-(n-Pentyl)-α-[p-(1,1,2,2-tetrafluoroethoxy)-phenyl]-3-pyrimidylmethane α-Ethyl-α-[p-(pentafluoroethoxy)phenyl]-5-pyrimidylmethane α-(p-Bromophenyl)-α-[p-(trifluoromethoxy)-phenyl]-3-pyridinemethanol α-[3,4-Difluoromethylenedioxy)phenyl]-α-(m-fluorophenyl)-5-pyrimidinemethanol α-(o-Chlorophenyl)-α-[p-(pentafluoroethoxy)-phenyl]-2-pyrazinemethanol α-(3-Pyridyl)-α-[p-(trifluoromethoxy)phenyl]-3-pyridinemethanol α-Cyclobutyl-α-methoxy-α-[p-(trifluoromethoxy)-phenyl]-2-methylpyrazine α-(Ethylthio)-α-(n-hexyl)-α-[p-(pentafluoroethoxy)-phenyl]-3-methylpyridine α-(Acetyloxy)-α-(n-propyl)-α-[p-(1,1,2,2-tetrafluoroethoxy)phenyl]-5-methylpyrimidine, and the like.

The novel nitrogen-containing heterocyclic compounds of this invention are prepared utilizing halo-substituted nitrogen-containing heterocycles as key starting materials. These particularly preferred starting materials are 5-bromopyrimidine, 2-iodopyrazine, and 3-bromopyridine. All of these compounds are compounds known to those skilled in the art, and the preparations thereof have been described in the literature. These particular halo compounds are preferred because of their ready availability and their excellent reactivity in the condensation reactions.

Both the novel pyrimidine and the pyrazine compounds useful in the novel methods and compositions of this invention can be synthesized by proceeding in general according to the preparative method taught in Belgian Patent No. 714,003. Following that method, in general, a suitable ketone, for example, isopropyl p-trifluoromethoxyphenyl ketone and 5-bromopyrimidine, or 2-iodopyrazine, are dissolved in a solvent composed of equal volumes of tetrahydrofuran and ethyl ether. The solution is cooled to −70° C., and while being maintained at that temperature, a solution of n-butyllithium in n-hexane is added. The reaction mixture is stirred overnight in the cold (−60° to −70° C.) The reaction product mixture is then worked up. It is washed successively with dilute aqueous ammonium chloride solution and water, and the organic layer is separated and dried over a suitable drying agent. The dried organic layer is concentrated to dryness in vacuo and the residue is chromatographed on a silica column using acetone-benzene diluent. The desired product is eluted from the column using a suitable eluent, for example, one composed of 10 percent acetone and 90 percent benzene by volume. The eluate, which contains the product, is concentrated in vacuo. The product, a heavy oil, is identified by elemental analyses, NMR, and IR spectra, as α-isopropyl-α-[p-(trifluoromethoxy)phenyl]-5-pyrimidinemethanol, or α-isopropyl-α-[p-(trifluoromethoxy)phenyl]-2-pyrazinemethanol, depending on the starting nitrogen heterocycle.

The preparation of the substituted 3-pyridine compounds is carried out in a slightly different manner. A solvent composed of equal volumes of tetrahydrofuran and ethyl ether is cooled to a temperature of about −30° to −40° C., the n-hexane solution of n-butyllithium is added thereto, and the whole cooled to a temperature of about −70° C. The 3-bromopyridine is dissolved in a suitable solvent, preferably anhydrous ethyl ether, and this ether solution is added dropwise to the tetrahydrofuran-ether solution of the n-butyllithium, while maintaining the temperature at about −70° C. A suitable ketone, for example, isopropyl p-trifluoromethoxyphenyl ketone, dissolved in anhydrous tetrahydrofuran-ethyl ether mixture (1:1), is then added to the reaction mixture. The remainder of the preparation and work-up proceeds as described supra, for the pyrimidine and pyrazine compounds. In the present instance, the product obtained is identified as α-isopropyl-α-[p-(trifluoromethoxy)phenyl]-3-pyridinemethanol, by elemental analyses and NMR spectrum.

Those compounds in the above generic formula I where X is $C_1-C_4$ alkoxy can be prepared by allowing an alkali-metal lower alkoxide such as sodium methoxide, potassium ethoxide, sodium propoxide, potassium butoxide, sodium butoxide, or the like, to react in the corresponding alkanol as solvent with a halo analogue of the desired product, for example, 5-[α-chloro-α-cyclohexyl-3,4-(difluoromethylenedioxy)benzyl]-pyrimidine (prepared according to the procedure outlined in Belgian Patent No. 714,003), to yield the desired product, α-loweralkoxy-α-cyclohexyl-α-[3,4-(difluoromethylenedioxy)phenyl]-5-pyrimidylmethane.

Those compounds where X is $C_1-C_4$ alkylthio can be prepared by allowing a suitable $C_1-C_4$ alkyl mercaptan to react with a halo analogue of the desired product, for example 2-[α-chloro-α-isopropyl-p-(trifluoromethoxy)benzyl]pyrazine (prepared according to the procedure set forth by Taylor et al., U.S. Pat. No. 3,544,682 (Dec. 1, 1970)), in the presence of triethylamine, to yield the desired $C_1-C_4$ alkylthio substituted product, α-loweralkylthio-α-isopropyl-α-[p-(trifluoromethoxy)phenyl]-2-pyrazylmethane.

In the case where X is $C_1-C_4$ alkanoyloxy, the compound can be prepared by allowing a mixture of the halo analogue of the desired product, for example, 3-[α-chloro-α-isopropyl-p-(trifluoromethoxy)benzyl]-pyridine (prepared according to the procedure set forth in Van Heyningen, U.S. Pat. No. 3,396,224 (Aug. 6, 1968)), with glacial acetic acid, for example, in the presence of anhydrous sodium acetate, to yield the desired product, α-loweralkanoyloxy-α-isopropyl-α-[p-(trifluoromethoxy)phenyl]-3-pyridylmethane. It will be obvious to one skilled in the art that other organic acids or organic acid anhydrides may be used for preparation of these alkanoyloxy derivatives of the methanol compounds.

When X is H in the generic formula I, supra, the compounds can be prepared according to the procedure of Sperber et al., U.S. Pat. No. 2,727,895 Dec. 20, 1955), whereby the 5-substituted pyrimidinemethanol, 2-substituted pyrazinemethanol, or 3-substituted pyridinemethanol (prepared as set forth above) is heated in a mixture of glacial acetic acid and 47 percent aqueous hydriodic acid to reduce the hydroxy group and yield, respectively, the 5-substituted pyrimidinemethane, 2-substituted pyrazinemethane, or 3-substituted pyridinemethane.

The nonphytotoxic acid addition salts of the above-prepared compounds are readily prepared, by methods well known to the art, from those novel compounds which are sufficiently basic. Thus, the free base is dissolved in ether, the solution cooled and saturated with, for example, anhydrous hydrogen chloride gas. The hydrochloric acid addition salt of the substituted compound precipitates and is filtered off and purified by recrystallization.

The ketone intermediates used in the preparation of the above-described novel compounds of this invention are themselves novel compounds of the formula

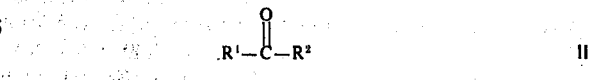

II wherein $R^1$ and $R^2$ are identified in the same manner as set forth hereinabove for formula I.

The preparations of these novel ketones are accomplished according to a number of procedures appearing in the prior art. Thus, the preparation of isopropyl p-trifluoromethoxyphenyl ketone is carried out by he procedure of Sheppard, Jour. Org. Chem. 29, 1 (1964). Following the same general procedure, other related ketones are readily prepared.

The preparation of ketones containing the 3,4-(difluoromethylenedioxy)phenyl moiety is accomplished by first synthesizing 3,4-(difluoromethylenedioxy)-bromobenzene according to the procedure of Stogryn, Jour. Org. Chem. 37, 673, (1972). This substituted bromobenzene is then allowed to react with an aldehyde, for example, isobutyraldehyde, in the presence of n-butyllithium, at about −40° C., to yield the intermediate alcohol, isopropyl 3,4-(difluoromethylenedioxy)-phenyl carbinol. This alcohol is oxidized using chromium trioxide in aqueous acetic acid to yield isopropyl 3,4-(difluoromethylenedioxy)phenyl ketone. Additional 3,4-(difluoromethylenedioxy)phenyl substituted ketones, alkyl or aryl, can be prepared in the same general manner.

The preparation of pentafluoroethoxy-substituted phenyl alkyl ketones is accomplished following the procedure of Belous et al., *J. Org. Chem.* (U.S.S.R.) 7, 1521 (1971). According to that procedure p-bromophenol is allowed to react with trifluoroacetic anhydride in the presence of sulfur tetrafluoride and hydogen fluoride, to yield pentafluoroethoxy-4-bromobenzene. This compound is allowed to react with isobutyraldehyde in the presence of n-butyllithium to yield the intermediate alcohol, isopropyl p-(pentafluoroethoxy)-phenyl carbinol. This alcohol is oxidized with chromium trioxide in the presence of aqueous acetic acid to yield the ketone, isopropyl p-(pentafluoroethoxy)phenyl ketone.

The compound, 1,1,2,2-tetrafluoroethoxy-4-bromobenzene, is commercially available. It is used to prepare a Grignard reagent, which is in turn allowed to react with isobutyronitrile to yield one of the desired ketones, isopropyl p-(1,1,2,2-tetrafluoroethoxy)phenyl ketone. Other p-(1,1,2,2-tetrafluoroethoxy)phenyl substituted alkyl or aryl ketones are prepared in the same general manner.

For the preparation of a ketone such as isopropyl 2,2,4,4-tetrafluoro-1,3-benzodioxan-6-yl ketone, the procedure disclosed in U.S. Pat. No. 3,632,820 (Jan. 4, 1972), Example 6, is used to prepare the intermediate halobenzodioxane. According to that reference, fluoroformic acid 2-trichloromethyl-4-chlorophenyl ester is allowed to react with anhydrous hydrofluoric acid to yield 2,2,4,4-tetrafluoro-6-chloro-1,3-benzodioxane. This compound can then be utilized to prepare the isopropyl 2,2,4,4-tetrafluoro-1,3-benzodioxan-6-yl or related alkyl or aryl ketones by any of the methods set forth above for the other ketones.

The syntheses of these novel intermediate ketones are set forth hereinbelow.

PREPARATION 1

Isopropyl p-trifluoromethoxyphenyl ketone

Using about 800 ml. of anhydrous tetrahydrofuran as solvent, the Grignard reagent was prepared from 50 g. of p-bromophenyltrifluoromethyl ether and 5.5 g. of magnesium turnings. To the Grignard reagent thus prepared, 15 g. of isobutyronitrile was added slowly, dropwise. The addition of the nitrile required about one-half hour. The reaction mixture was heated to refluxing for about 10 hours, cooled, and decomposed by the addition of aqueous 1N hydrochloric acid with stirring, to a pH of approximately 3. The aqueous layer was separated from the organic layer and the aqueous layer was discarded. The organic layer was dried over anhydrous magnesium sulfate. The drying agent was then filtered off and the filtrate was concentrated in vacuo. The residue was distilled to yield a liquid product having a boiling point of about 97°–98° C., at house vacuum pressure. The product weighed 19 g. It was identified by infrared spectrum as isopropyl p-trifluoromethoxyphenyl ketone.

PREPARATION 2

Isopropyl p-pentafluoroethoxyphenyl ketone

Starting with 4-bromophenol, the preparation of 4-bromopentafluoroethoxybenzene was carried out following the procedure of Belous et al., *J. Org. Chem.* (U.S.S.R.) 7, 1521 (1971).

To a solution of 15 g. of the thus prepared 4-bromopentafluoroethoxybenzene in 200 ml. of anhydrous ethyl ether, was added 25 ml. of a 22 percent solution of n-butyllithium in n-hexane. The mixture was cooled to about −60° C., and while being maintained at this temperature, to the mixture was added slowly a solution of 10 g. of isobutyraldehyde in 200 ml. of anhydrous ethyl ether. The reaction mixture was maintained at about −60° C., and stirred overnight, followed by stirring for a period of 48 hours at room temperature.

The reaction product mixture was worked up by the addition of aqueous ammonium chloride solution. The organic phase was separated and dried over anhydrous magnesium sulfate. The drying agent was filtered off. The filtrate was concentrated in vacuo to yield product having a weight of about 23 g. The product was identified by infrared spectrum as isopropyl p-pentafluoroethoxyphenyl carbinol.

The carbinol thus prepared, 20 g., was dispersed in 200 ml. of glacial acetic acid with stirring, and to the mixture was added 20 g. of chromium trioxide dissolved in 30 ml. of water. The addition was carried out carefully and the reaction temperature was kept below 80°C. Stirring of the mixture was continued for 4 hours. The reaction product mixture was cooled and poured onto a mixture of crushed ice and aqueous 50 percent sodium hydroxide solution, and the pH adjusted to pH 8. The mixture was extracted with large volumes of ether, and the ether extracts combined and washed with dilute aqueous sodium hydroxide solution. The ether solution was dried and concentrated in vacuo. The residue was chromatographed over a silica column using benzene as solvent and eluent, to yield 7 g. of product which was identified by NMR and infrared spectra as isopropyl p-pentafluoroethoxyphenyl ketone.

PREPARATION 3

3,4-(Difluoromethylenedioxy)phenyl isopropyl ketone

A mixture of 50 g. of 3,4-(methylenedioxy)bromobenzene and 200 g. of phosphorus pentachloride was heated at about 80°C. for about 4 hours. At the end of this time, the reaction product mixture was distilled and the material boiling at 115°–125°C. was collected. It weighed about 42 g. and was identified by NMR spectrum as 3,4-(dichloromethylenedioxy)bromobenzene.

A mixture of 3,4-(dichloromethylenedioxy)bromobenzene, 42 g., and 28 g. of antimony trifluoride was heated under reduced pressure. At approximately 80°–82°C., the product distilled over, and there was collected 34 g. of product identified by elemental analyses as 3,4-(difluoromethylenedioxy)bromobenzene.

To 56 g. of 3,4-(difluoromethylenedioxy)bromobenzene in 250 ml. of tetrahydrofuran was added 110 ml. of a 22 percent solution of n-butyllithium in n-hexane at −70°C., in an atmosphere of nitrogen. To this mixture was added 16 g. of isobutyraldehyde, and the reaction mixture was stirred overnight at about −70°C. The reaction product mixture was worked up by pouring it into a concentrated aqueous ammonium chloride solution with stirring. The organic layer was separated and dried. The drying agent was filtered off and and the organic solvent removed in vacuo. A total of 27 g. of the crude carbinol, 3,4-(difluoromethylenedioxy)phenyl isopropyl carbinol, was obtained and used without further purification in the next step.

Following the same general procedure as described in Preparation 2, the carbinol, 27 g., was oxidized with chromium trioxide in glacial acetic acid, to yield 3,4-(difluoromethylenedioxy)phenyl isopropyl ketone, weighing 16 g. and identified by NMR spectrum.

PREPARATION 4

Cyclohexyl 3,4-(difluoromethylenedioxy)phenyl ketone

To a solution of 24 g. of 3,4-(difluoromethylenedioxy)bromobenzene in 250 ml. of ether was added 2.4 g. of magnesium shavings. To the Grignard reagent thus prepared was added 11 g. of cyclohexylcarboxaldehyde in 50 ml. of anhydrous ethyl ether. The reaction mixture was allowed to stir for about 2–3 hours. The reaction product mixture was worked up by adding to it at room temperature a concentrated aqueous solution of ammonium chloride. The organic layer was separated, dried, filtered from the drying agent, and concentrated in vacuo. The residue, which is the crude carbinol, was oxidized with chromium trioxide and glacial acetic acid. The oxidation was worked up by pouring onto a mixture of crushed ice and 50 percent aqueous sodium hydroxide. The mixture was extracted with ethyl ether. The ether solution was dried, the drying agent filtered off, and the filtrate concentrated in vacuo. The residue thus obtained was dissolved in benzene and chromatographed over a silica column using benzene as the eluent. There was obtained 8 g. of cyclohexyl 3,4-(difluoromethylenedioxy)phenyl ketone, identified by its infrared and NMR spectra.

Following the same general procedure set forth above and using suitable starting materials, additional ketones were prepared:

3,4-(Difluoromethylenedioxy)phenyl undecyl ketone. Melting point: oil. Identified by infrared spectrum.

3-Chloro-4'-tetrafluoroethoxybenzophenone. Melting point: oil. Identified by infrared spectrum.

3-Pyridyl p-tetrafluoroethoxyphenyl ketone. Melting point: oil. Identified by infrared spectrum.

The following examples describe in detail the methods used in preparing the novel substituted nitrogen-containing heterocyclic compounds of this invention. However, the invention is not be construed as limited thereby, either in spirit or in scope, since it will be apparent to those skilled in the art that many modifications both of materials and methods may be practiced within the purpose and intent of this disclosure.

EXAMPLE 1

α-Isopropyl-α-[p-(trifluoromethoxy)phenyl]-5-pyrimidinemethanol

To a solution of 19 g. (0.082 mole) of isopropyl p-trifluoromethoxyphenyl ketone, in 250 ml. of a mixture of equal volumes of tetrahydrofuran and ethyl ether was added a solution of 32 g. (0.1 mole) of 5-bromopyrimidine in 350 ml. of tetrahydrofuran-ethyl ether, and the mixture was cooled to −70°C., in an atmosphere of dry nitrogen gas. The mixture was stirred and maintained at about −70°C., in the atmosphere of dry nitrogen gas, while there was added 60 ml. of a 15 percent solution of n-butyllithium in n-hexane. The resulting reaction mixture was maintained at about −70°C., with stirring for a period of about 8 hours.

The reaction product mixture was allowed to warm to room temperature. Aqueous ammonium chloride solution was added, and the aqueous and organic layers were separated. The organic layer was washed with water and dried over anhydrous magnesium sulfate. The drying agent was filtered off and the filtrate was concentrated in vacuo to yield an oil weighing about 33 g. This oil was chromatographed on a silica column, and the desired product was eluted from the column using a solvent mixture of 10 percent acetone and 90 percent benzene by volume. The acetone-benzene eluate was concentrated in vacuo, to yield a heavy oil weighing about 14 g. This heavy oil was identified by NMR and infrared spectra, and elemental analyses, as α-isopropyl-α-[p-(trifluoromethoxy)phenyl]-5-pyrimidinemethanol.

Following the same general procedure set forth hereinabove, and using suitable starting materials, the following additional compounds were synthesized:

α-Isopropyl-α-[p-(1,1,2,2-tetrafluoroethoxy)phenyl]-5-pyrimidinemethanol. Melting point: dark α-Cyclohexyl-α-[p-(1,1,2,2-tetrafluoroethoxy)phenyl]-5-pyrimidinemethanol. Melting point: oil. Structure identified by NMR spectrum.

α-n-Hexyl-α-[p-(1,1,2,2-tetrafluoroethoxy)phenyl]-5-pyrimidinemethanol. Melting point: oil. Structure identified by NMR spectrum.

α-(m-Chlorophenyl)-α-[p-(1,1,2,2-tetrafluoroethoxy)phenyl]-5-pyrimidinemethanol. Melting point: oil. Structure identified by NMR spectrum.

EXAMPLE 2

α-Cyclohexyl-α-[3,4-(difluoromethylenedioxy)phenyl]-5-pyrimidinemethanol

To a solution of 8 g. of cyclohexyl 3,4-(difluoromethylenedioxy)phenyl ketone, in 125 ml. of a mixture of equal volumes of tetrahydrofuran and ethyl ether, was added a solution of 4.7 g. of 5-bromopyrimidine in 50 ml. of tetrahydrofuran-ethyl ether, and the mixture was cooled to −70°C., in an atmosphere of dry nitrogen gas. The mixture was stirred and maintained at about −70°C., in the atmosphere of dry nitrogen gas, while there was added 13 ml. of a 15 percent solution of n-butyllithium in n-hexane. The resulting reaction mixture was maintained at −70°C., while being stirred for a period of about 8 hours.

The reaction product mixture was allowed to warm to room temperature. Aqueous ammonium chloride solution was added and the aqueous organic layers were separated. The organic layer was washed with water and dried over anhydrous magnesium sulfate. The drying agent was filtered off and the filtrate was concentrated to yield a crude product having a weight of about 7 g. This crude product was chromatographed on a silica column, and the desired product was eluted from the column using a solvent mixture of 10 percent acetone and 90 percent benzene by volume. The eluate was concentrated in vacuo and the residue became a solid glass, having a melting point of about 64°C. It was identified by NMR spectrum as α-cyclohexyl-α-[3,4-(difluoromethylenedioxy)phenyl]-5-pyrimidinemethanol.

Following the same general procedure set forth above and using suitable starting materials, the following additional compounds were prepared:

α-[3,4-(Difluoromethylenedioxy)phenyl]-α-isopropyl-5-pyrimidinemethanol. Melting point: 127°C. Structure confirmed by NMR spectrum and elemental analyses.

α-[3,4-(Difluoromethylenedioxy)phenyl]-α-undecyl-5-pyrimidinemethanol. Melting point: oil. Structure identified by NMR spectrum.

EXAMPLE 3

α-Isopropyl-α-[p-(trifluoromethoxy)phenyl]-2-pyrazinemethanol

To a solution of 9 g. of isopropyl p-trifluoromethoxyphenyl ketone in 300 ml. of ethyl ether, was added a solution of 10 g. of 2-iodopyrazine in 300 ml. of ethyl ether, and the mixture was cooled to a −70°C., in an atmosphere of dry nitrogen gas. The mixture was stirred and maintained at about −70°C., in the atmosphere of dry nitrogen gas, while there was added 25 ml. of a 15 percent solution of n-butyllithium in n-hexane. The resulting reaction mixture was maintained at −70°C., while being stirred overnight.

The reaction product mixture was allowed to warm to room temperature. Aqueous ammonium chloride solution was added and the aqueous and organic layers were separated. The organic layer was washed with water and dried over anhydrous magnesium sulfate. The drying agent was filtered off and the filtrate was concentrated to yield an oil. This oil was chromatographed on a silica column, and the desired product was eluted from the column using a solvent mixture of 5 percent acetone and 95 percent benzene by volume. The acetone-benzene eluate was concentrated in vacuo, to yield a heavy oil which upon standing solidified. The solid had a melting point of about 70°C., and was identified by NMR spectrum and elemental analyses as α-isopropyl-α-[p-(trifluoromethoxy)phenyl]-2-pyrazinemethanol.

Following the same general procedure set forth hereinabove and using suitable starting materials, the following additional compounds were synthesized:

α-(3-Pyridyl)-α-[p-(1,1,2,2-tetrafluoroethoxy)-phenyl]-2-pyrazinemethanol. Melting point: oil. Structure identified by NMR spectrum.

α-Isopropyl-α-[p-(1,1,2,2-tetrafluoroethoxy)-phenyl]-2-pyrazinemethanol. Melting point: oil. Structure identified by NMR spectrum.

EXAMPLE 4

α-Isopropyl-α-[p-(trifluoromethoxy)phenyl]-3-pyridinemethanol

To a solution of 250 ml. of a mixture of equal volumes of tetrahydrofuran and ethyl ether, cooled to about −30° to about −40°C., and maintained under an atmosphere of dry nitrogen gas, was added 50 ml. of a 15 percent solution of n-butyllithium in n-hexane. The mixture was stirred and cooled to about −70°C, and there was added thereto a solution of 16 g. of 3-bromopyridine in 250 ml. of the 50:50 by volume mixture of tetrahydrofuran and ethyl ether. After the addition was complete, the reaction mixture was allowed to stir for about one-half hour. A solution of 20 g. of isopropyl p-trifluoromethoxyphenyl ketone in 100 ml. of the mixture of tetrahydrofuran and ethyl ether was then added dropwise with stirring. The resulting reaction mixture was maintained at −70°C. while being stirred overnight.

The reaction product mixture was allowed to warm to room temperature, and aqueous ammonium chloride solution was added. The aqueous and organic layers were separated. The organic layer was washed with water and dried over anhydrous magnesium sulfate. The drying agent was filtered off and the filtrate was concentrated to yield a yellow oil having a weight of about 43 g. This oil was chromatographed on a silica column, and the desired product was eluted from the column using a solvent mixture of 10 percent acetone and 90 percent benzene by volume. The acetone-benzene eluate was concentrated in vacuo, to yield a yellow oil weighing about 11 g. On standing, the oil solidified. The solid was recrystallized from hot ether to yield white crystals having a melting point of about 81°–82°C. The crystalline product was identified by NMR spectra as α-isopropyl-α-[p-(trifluoromethoxy)-phenyl]-3-pyridinemethanol.

Following the same general procedure set forth hereinabove and using suitable starting materials, the following compound was synthesized:

α-Cyclohexyl-α-[p-(1,1,2,2-tetrafluoroethoxy)-phenyl]-3-pyridinemethanol. Melting point: oil. Structure identified by NMR spectrum.

These novel fluoroalkoxyphenyl-substituted nitrogen heterocycles are active as herbicides, plant fungicides, and as plant growth regulators. Thus, it has been found that, for example, powdery mildew of cucumber is completely combatted by the application of a fungicidal composition containing 400 ppm. of a compound of generic formula I.

It has also been found that these novel fluoroalkoxyphenyl-substituted nitrogen heterocycles are especially effective in inhibiting internodal growth of plants when applied at rates within the range of about 0.125 to about 5 lbs./A. At these rates, there is no adverse effect or injury to the plants. Larger amounts can be used, but are not economically attractive. The exact amount of compound to be used will vary somewhat depending upon the activity of the particular compound being used and the sensitivity of the particular plant being treated.

The types of plants that have been found to be affected in this manner by these compounds include crop plants, ornamental plants, woody plants and turf. Specific examples of these types of plants include cucumber, soybean, chrysanthemum, wheat, oats, barley, corn, rye, flax, privet, rice, cotton, tomato and bluegrass.

While there is no wish to be bound to any theory as to the mode of activity of these compounds, it is believed that the compounds owe their activity to their unique properties as gibberellic acid antagonists. This would explain the broad spectrum activity of the compounds. In ex-plant assays designed to demonstrate gibberellic acid activity, the compounds have performed as antagonists at levels as low as about $10^{-5}$ M. Further, when both the inhibiting compound and gibberellic acid are applied to plants at the same time, growth-inhibiting effects are partially neutralized. The growth of inhibited plants is stimulated when gibberellic acid is applied anytime after application of the inhibitor.

It has been observed that root applications of these compounds have resulted in the greatest activity. However, other methods of application, such as foliar spray or seed treatment can be used with some degree of success. For application, the compounds are formulated into drenches, spray concentrates, wettable powders, dusts, etc., in accordance with procedures known in the art.

For any such uses, the compounds are formulated into compositions desirably containing, in addition to the fluoroalkoxyphenyl-substituted nitrogen heterocycle, one or more of a plurality of agriculturally-acceptable additaments, including water, polyhydroxy compounds, petroleum distillates, and other dispersion media, surface-active dispersing agents, emulsifiers, and finely-divided inert solids. The concentration of the particular fluoroalkoxyphenyl-substituted compound in these compositions may vary depending on whether the composition is intended as an emulsifiable concentrate or a wettable powder designed to be subsequently diluted with additional inert carrier, such as water, to produce the ultimate treating composition, or is intended for direct application as a dust to plants.

Thus, treating compositions are most conveniently formulated by preparing liquid or solid concentrates, which are subsequently diluted to the desired level for use.

Emulsifiable liquid concentrates can be prepared by incorporating from about 4.5 to about 24 percent by weight of the active ingredient and an emulsifying agent in a suitable water-immiscible organic liquid. Such concentrates may be further diluted with water to form spray mixtures in the form of oil-in-water emulsions. Such spray compositions then comprise active toxicant, water-immiscible solvent, emulsifying agent, and water. Suitable emulsifying agents can be of the nonionic or ionic types, or blends thereof, and include condensation products of alkylene oxides with phenols and organic acids, polyoxyethylene derivatives of sorbitan esters, complex ether-alcohols, ionics of the aralkyl sulfonate type, and the like. Suitable water-immiscible organic liquids to be employed include aromatic hydrocarbons, aliphatic hydrocarbons, cycloaliphatic hydrocarbons, and mixtures thereof such as petroleum distillates.

Solid concentrate mixtures can be prepared by incorporating from about 10 to about 50 percent by weight of the fluoroalkoxyphenyl-substituted nitrogen-heterocycle compound in a finely-divided inert solid carrier such as bentonite, fuller's earth, diatomaceous earth, hydrated silica, diatomaceous silica, expanded mica, talc, chalk, and the like. Such concentrates can be formulated, if desired, for direct use as dusting compositions, or can be diluted, if desired, with additional inert solid carriers to produce dusting powders containing around 0.05 to 1 percent by weight of the fluoroalkoxyphenyl-substituted compound. Alternatively, surfactants, that is, dispersing and/or wetting agents, can be incorporated along with the fluoroalkoxyphenyl-substituted compound in the solid carrier to form wettable powder concentrates ranging from 10 to 25 percent by weight concentration, which subsequently can be dispersed in water or other hydroxylated carrier to form spray compositions. Suitable surfactants include condensed aryl sulfonic acids and sodium salts thereof, sodium lignosulfate, sulfonate-oxide condensate blends, alkyl aryl polyether alcohols, sulfonate/nonionic blend, anionic wetting agents, and the like.

Further, the fluoroalkoxyphenyl-substituted nitrogen heterocycle compound can be incorporated in solutions, simple dispersions, aerosol formulations, and other media adaptable to be employed for treating vegetation or applying to the soil.

The rate of application of these novel compounds will vary with the particular compound being employed and the plant being treated. In general, the compound should be applied at a rate within the range of about 0.125 to about 5 pounds per acre, and preferably within the range of about 0.125 to about 2 pounds per acre. As discussed above, the mode of application also affects the degree of activity and could result in differences in the effective amount. The preferred method of application of the instant novel compounds is as a soil drench. Not surprisingly, it has been found that mature plants are not as susceptible as immature ones.

The following experiment will illustrate the growthinhibiting activity of these novel compounds.

EXPERIMENT

The growth regulator activity of a number of representative compounds coming within the scope of the generic formula, supra, was tested in the following manner.

Plant growth regulator compositions were prepared by dissolving 62.5 mg. of test compound in 1 ml. of acetone:ethanol (1:1 by volume) and adding 24 ml. of an aqueous mixture of a sulfonate emulsifier and a nonionic emulsifier, to give a final volume of 25 ml., with a test compound concentration of 2500 ppm. This composition was then serially diluted by a factor of 5, with the aqueousemulsifier mixture, to give 500 and 100 ppm. solutions.

Foliar sprays were applied with a DeVilbiss atomizer operated at 10 to 12 psi. Soil drenches were poured into the pot as rapidly as possible without overflowing.

Soybeans, variety Amsoy, were planted in 4-inch square plastic pots and thinned to one plant per pot shortly after emergence. Bluegrass, variety Kentucky, was planted in 3-inch square plastic pots in sterile soil. Chrysanthemums, variety Princess Ann, purchased as rooted cuttings of genetically pure stock, were transplanted upon receipt into 4-inch square plastic pots. Standard greenhouse soil (½ Brookston silty loam and ½ coarse sand by volume) was used.

Treatments were applied after the chrysanthemums had been established in the pots for about 8 to 15 days; after the soybeans had reached 9 to 11 days of age, when the first trifoliate had fully expanded; and after the bluegrass was 20 to 30 days old.

Fertilizer applications were made weekly using a hose-end proportioner to apply 6.7 g./gallon of 23-19-17 Rapid-Gro soluble fertilizer during routine hand watering.

A reference standard, α-cyclopropyl-α-(4-methoxyphenyl)-5-pyrimidinemethanol, was used, and it was formulated and applied in the same manner and rates as the test compounds. Six or more untreated plants of each species were included as controls.

Bluegrass was clipped to a height of one-half inch one day before treatment and again approximately one week after treatment.

Observations were made on bluegrass and chrysanthemums 25 days after treatment, and on soybeans 15 to 25 days after treatment, depending on growing conditions (during cloudy weather, soybeans eliolate and must be read out early).

The test chemicals, formulated as described above, were applied to Amsoy soybeans, Princess Ann chrysanthemums, and Kentucky bluegrass, by both foliar spray and soil drench, at three rates for each mode of application. Duplicate sets of untreated controls were employed. The growth of the treated plants was compared to the controls and the degree of inhibition noted by a numbering system having the following meaning:

+3 = Distinct promotion
+2 = Moderate promotion
+1 = Slight promotion
0 = No effect
−1 = Slight inhibition
−2 = Moderate inhibition
−3 = Severe inhibition The average results from the two sets of plants treated with each of the test compounds are reported in the following charts. Chart 1 sets forth the results of the soil drench treatment, and Chart 2 the results of the foliar spray treatment. In both charts, column 1 lists the test compounds, column 2, the application rate in pounds per acre (Chart 1), and parts per million (ppm., Chart 2); columns 3, 4, and 5, list the test plants and the degree of growth inhibition observed.

CHART 1

| Compound | Rate lb./A. | Soybean | Drench Bluegrass | Mum |
|---|---|---|---|---|
| α-Isopropyl-α-[p-(trifluoromethoxy)phenyl]-5-pyrimidinemethanol | 0.4<br>2.0<br>10.0 | 0<br>0<br>−1.5 | −1<br>−2<br>−3 | 0<br>0<br>−2.5 |
| α-Isopropyl-α-[p-(1,1,2,2-tetrafluoroethoxy)phenyl]-2-pyrazinemethanol | 0.4<br>2.0<br>10.0 | −2<br>−3<br>−3 | −2<br>−3<br>−3 | 0<br>−1<br>−2 |
| α-Isopropyl-α-[p-trifluoromethoxy)phenyl]-2-pyrazinemethanol | 0.4<br>2.0<br>10.0 | 0<br>−1<br>−1 | −1<br>−2<br>−3 | 0<br>−1<br>−3 |
| α-Isopropyl-α-[p-(pentafluoroethoxy)phenyl]-5-pyrimidinemethanol | 0.4<br>2.0<br>10.0 | −2<br>−2<br>−3 | −1<br>−2<br>−3 | −1<br>−2<br>−3 |
| α-n-Propyl-α-[p-(trifluoromethoxy)phenyl]-5-pyrimidinemethanol | 0.4<br>2.0<br>10.0 | −2<br>−1<br>−2 | 0<br>−1<br>−3 | −1<br>−2<br>−3 |
| α-Phenyl-α-[p-(1,1,2,2-tetrafluoroethoxy)phenyl]-5-pyridinemethanol | 0.4<br>2.0<br>10.0 | 0<br>−2<br>−3 | 0<br>0<br>−3 | 0<br>0<br>−1 |
| α-Isopropyl-α-[p-(trifluoromethoxy)phenyl]-5-pyrimidinemethanol | 0.4<br>2.0<br>10.0 | −2<br>−2<br>−3 | −1<br>−2.5<br>−3 | −1.5<br>−2<br>−2 |
| α-Isopropyl-α-[p-(1,1,2,2-tetrafluoroethoxy)phenyl]-5-pyrimidinemethanol | 0.4<br>2.0<br>10.0 | −2<br>−3<br>−3 | 0<br>−1<br>−3 | −2<br>−3<br>−3 |
| α-[3,4-(Difluoromethylenedioxy)phenyl]-α-isopropyl-5-pyrimidinemethanol | 0.4<br>2.0<br>10.0 | −2<br>−2<br>−2 | 0<br>−2<br>−3 | −1<br>−2<br>−2 |
| α-[3,4-(Difluoromethylenedioxy)phenyl]-α-undecyl-5-pyrimidinemethanol | 0.4<br>2.0<br>10.0 | 0<br>0<br>0 | 0<br>0<br>0 | 0<br>0<br>−1 |
| α-Cyclohexyl-α-[3,4-(difluoromethylenedioxy)phenyl]-5-pyrimidinemethanol | 0.4<br>2.0<br>10.0 | 0<br>−2<br>0 | 0<br>0<br>−3 | 0<br>0<br>0 |
| α-Cyclohexyl-α-[p-(1,1,2,2-tetrafluoroethoxy)phenyl]-5-pyrimidinemethanol | 0.4<br>2.0<br>10.0 | 0<br>0<br>0 | 0<br>−3<br>−3 | 0<br>0<br>−3 |

CHART 1-continued

| Compound | Rate lb./A. | Soybean | Drench Bluegrass | Mum |
|---|---|---|---|---|
| α(n-Hexyl)-α-[p-(1,1,2,2-tetrafluoroethoxy)phenyl]-5-pyrimidinemethanol | 0.4<br>2.0<br>10.0 | 0<br>0<br>0 | 0<br>0<br>−2 | 0<br>0<br>0 |
| Controls | 0 | 0 | 0 | 0 |

CHART 2

| Compound | Rate ppm. | soybean | Spray Bluegrass | Mum |
|---|---|---|---|---|
| α-Isopropyl-α-[p-(trifluoromethoxy)phenyl]-3-pyridinemethanol | 100<br>500<br>2500 | 0<br>−1<br>−1 | 0<br>−1.5<br>−3 | −1.5<br>−2<br>−3 |
| α-Isopropyl-α-[p-(1,1,2,2-tetrafluoroethoxy)phenyl]-2-pyrazinemethanol | 100<br>500<br>2500 | −2<br>−3<br>−3 | 0<br>−3<br>−3 | −1<br>−3<br>−3 |
| α-Isopropyl-α-[-p(trifluoromethoxy)phenyl]-2-pyrazinemethanol | 100<br>500<br>2500 | 0<br>−1<br>−2 | −1<br>−2<br>−3 | −1<br>−2<br>−2 |
| α-Isopropyl-α-[p-(pentafluoroethoxy)phenyl]-5-pyrimidinemethanol | 100<br>500<br>2500 | −2<br>−3<br>−3 | 0<br>−2<br>−3 | −2<br>−3<br>−3 |
| α-n-Propyl-α-[p-trifluoromethoxy)phenyl]-5-pyrimidinemethanol | 100<br>500<br>2500 | −1<br>−3<br>−3 | 0<br>0<br>−2 | −2<br>−2<br>−3 |
| α-Phenyl-α-[p-(1,1,2,2-tetrafluoroethoxy)phenyl]-5-pyrimidinemethanol | 100<br>500<br>2500 | 0<br>−1<br>−3 | 0<br>0<br>0 | 0<br>0<br>0 |
| α-Isopropyl-α-[p-(trifluoromethoxy)phenyl]-5-pyrimidinemethanol | 100<br>500<br>2500 | −2<br>−2.5<br>−2.5 | −1<br>−2<br>−2.5 | −2<br>−2<br>−2.5 |
| α-Isopropyl-α-[p-(1,1,2,2-tetrafluoroethoxy)phenyl]-5-pyrimidinemethanol | 100<br>500<br>2500 | −1<br>−2<br>−3 | 0<br>−1<br>−3 | −2<br>−3<br>−3 |
| α-[3,4-(Difluoromethylenedioxy)phenyl]-α-isopropyl-5-pyrimidinemethanol | 100<br>500<br>2500 | 0<br>0<br>−2 | 0<br>−1<br>−3 | 0<br>−1<br>−1 |
| α-Cyclohexyl-α-[p-(1,1,2,2-tetrafluoroethoxy)phenyl]-5-pyrimidinemethanol | 100<br>500<br>2500 | 0<br>0<br>0 | −1<br>−2<br>−3 | −1<br>0<br>−3 |
| Controls | 0 | 0 | 0 | 0 |

It is not unexpected that the activity of these compounds as plant growth regulators varies depending on the plants treated and the method used for applying the growth regulating composition, whether by spray, or by drench, and further, that not every compound is active by every method of application.

We claim:

1. A method of inhibiting the internodal growth of plants which comprises contacting the plants selected from the group consisting of crop plants, ornamental plants, and turf, with an effective growth inhibiting amount of a compound of the formula

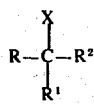

wherein
R is 5-pyrimidinyl;
R$^1$ is isopropyl;
R$^2$ is trifluoromethoxyphenyl, tetrafluoroethoxyphenyl or pentafluoroethoxyphenyl;
X is hydroxy;
and the nonphytotoxic acid addition salts thereof.

2. The method of claim 1 wherein the compound is applied at the rate of from about 0.125 to about 5 lbs. per acre.

3. The method of claim 1 wherein the compound is applied at the rate of from about 0.125 to about 2 lbs. per acre.

4. The method of claim 1 wherein the active compound is α-isopropyl-α-[p-(trifluoromethoxy)phenyl]-5-pyrimidinemethanol.

5. The method of claim 1 wherein the active compound is α-isopropyl-α-[p-(pentafluoroethoxy)phenyl]-5-pyrimidinemethanol.

6. The method of claim 1 wherein the active compound is α-[3,4-(difluoromethylenedioxy)phenyl]-α-isopropyl-5-pyrimidinemethanol.

7. The method of claim 1 wherein the growth-inhibiting compound is used in the form of a composition comprising an effective amount of a compound of the formula

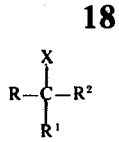

wherein
R is 5-pyrimidinyl;
R$^1$ is isopropyl;
R$^2$ is trifluoromethoxyphenyl, tetrafluoroethoxyphenyl, or pentafluoroethoxyphenyl;
X is hydroxy;
and the nonphytotoxic acid addition salts thereof, an agriculturally-acceptable inert carrier, and a dispersing agent.

8. A growth-inhibiting composition comprising an effective growth-inhibiting amount of a compound of the formula

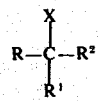

wherein
R is 5-pyrimidinyl;
R$^1$ is isopropyl;
R$^2$ is trifluoromethoxyphenyl, tetrafluoroethoxyphenyl, or pentafluoroethoxyphenyl;
X is hydroxy;
and the nonphytotoxic acid addition salts thereof, an agriculturally-acceptable inert carrier, and a dispersing agent.

9. A composition as defined in claim 8 wherein the compound is α-isopropyl-α[p-(trifluoromethoxy)phenyl]-5-pyrimidinemethanol.

* * * * *

UNITED STATES PATENT AND TRADEMARK OFFICE
CERTIFICATE OF CORRECTION

PATENT NO. : 3,967,949
DATED : July 6, 1976
INVENTOR(S) : Robert L. Benefiel et al.

It is certified that error appears in the above-identified patent and that said Letters Patent are hereby corrected as shown below:

Column 10, line 25, after the word "dark" the following was omitted  --brown oil.  Structure identified by NMR spectrum. --

Column 10, after line 25, the following compounds were omitted.

-- α-Isopropyl-α-[p-(pentafluoroethoxy)phenyl]-5-pyrimidinemethanol.  Melting point:  oil.  Structure identified by NMR spectrum.

α-(n-Propyl)-α-[p-(trifluoromethoxy)phenyl]-5-pyrimidinemethanol.  Melting point:  94-95°C. Structure identified by elemental analyses and NMR spectrum.

α-Phenyl-α-[p-1,1,2,2-tetrafluoroethoxy)phenyl]-5-pyrimidinemethanol.  Melting point:  glass. Structure identified by elemental analyses and NMR spectrum. --

Column 15, line 46, "5-pyridinemethanol" should read -- 5-pyrimidinemethanol --.

Signed and Sealed this

Twelfth Day of October 1976

[SEAL]

Attest:

RUTH C. MASON
Attesting Officer

C. MARSHALL DANN
Commissioner of Patents and Trademarks